United States Patent
Deane et al.

(10) Patent No.: US 7,708,802 B1
(45) Date of Patent: May 4, 2010

(54) GAS FRACTIONALIZATION APPARATUS WITH BUILT-IN ADMINISTRATIVE AND SELF-DIAGNOSTIC FUNCTIONS

(75) Inventors: Geoffrey Frank Deane, Goleta, CA (US); Jeffrey Jenneve, Santa Barbara, CA (US); Michael Ricci, Camarillo, CA (US); Brenton Alan Taylor, Kenwood, CA (US)

(73) Assignee: Inogen, Inc., Goleta, CA (US)

( * ) Notice: Subject to any disclaimer, the term of this patent is extended or adjusted under 35 U.S.C. 154(b) by 963 days.

(21) Appl. No.: 11/438,897

(22) Filed: May 23, 2006

Related U.S. Application Data

(60) Provisional application No. 60/684,144, filed on May 23, 2005.

(51) Int. Cl.
 *B01D 46/46* (2006.01)
(52) U.S. Cl. .................. 95/19; 95/1; 95/8; 96/417; 96/421; 96/424; 116/200; 340/500
(58) Field of Classification Search .............. 96/417, 96/421, 424; 116/200; 340/500; 95/1, 8, 95/19
 See application file for complete search history.

(56) References Cited

U.S. PATENT DOCUMENTS

| | | | | |
|---|---|---|---|---|
| 3,800,586 A | * | 4/1974 | Delatorre et al. | 73/49.2 |
| 4,561,287 A | * | 12/1985 | Rowland | 95/11 |
| 4,627,860 A | | 12/1986 | Rowland | |
| 4,783,205 A | * | 11/1988 | Searle | 96/111 |
| 4,916,630 A | * | 4/1990 | Miller | 702/30 |
| 5,469,372 A | * | 11/1995 | McBrearty et al. | 702/182 |
| 5,858,063 A | | 1/1999 | Cao | |
| 5,931,159 A | * | 8/1999 | Suzuki et al. | 128/204.18 |
| 2002/0077858 A1 | | 6/2002 | Haines | |
| 2003/0130591 A1 | * | 7/2003 | Starr et al. | 600/538 |
| 2004/0187871 A1 | * | 9/2004 | Kimmel et al. | 128/204.23 |
| 2005/0103342 A1 | * | 5/2005 | Jorczak et al. | 128/205.24 |

* cited by examiner

*Primary Examiner*—Jason M Greene
*Assistant Examiner*—Anthony Shumate
(74) *Attorney, Agent, or Firm*—Knobbe, Martens, Olson & Bear, LLP

(57) ABSTRACT

A portable gas fractionalization system with built-in administrative and self-diagnostic functions is provided. The system includes a multiple mode programmable controller which has a operations mode and a diagnostic mode that can be activated by a triggering event. The triggering event can be when a user enters a command input, when one or more process parameters deviate from a nominal value, or when the system is scheduled to perform self-diagnostics. The system also includes a multi-level user interface which is integrally formed with the system. The user interface includes a multi-level display screen and a plurality of user command functions. The diagnostic information displayed on the display screen can be in an abbreviated code form so that only technicians would be able to interpret meaning of the code.

5 Claims, 3 Drawing Sheets

GAS FRACTIONALIZATION APPARATUS WITH BUILT-IN ADMINISTRATIVE AND SELF-DIAGNOSTIC FUNCTIONS

CROSS-REFERENCE TO RELATED APPLICATIONS

This application claims the benefit of priority under 35 U.S.C. §119(e) of U.S. Provisional Application No. 60/684,144 filed on May 23, 2005, which is hereby incorporated by reference in its entirety.

BACKGROUND OF THE INVENTION

1. Field of the Invention

This invention relates generally to gas fractionalization systems and, in particular, to gas fractionalization systems with built-in administrative and self-diagnostic functions.

2. Description of the Related Art

The application of oxygen concentrators for therapeutic use is known, and many variants of such devices exist. A particularly useful class of oxygen concentrators is designed to be portable, allowing users to move about and to travel to extended periods of time without the need to carry a supply of stored oxygen. Most of these portable concentrators produce an oxygen-rich gas by feeding compressed air through a pressure swing adsorption (PSA) system which selectively removes nitrogen and other components in the air so as to produce a pressurized, oxygen-rich product gas.

Generally, the design of such portable concentrators should be small, lightweight and quiet to be effective. The portable concentrators still need to produce a prescribed flow rate of oxygen. Portable concentrators involve a significant amount of miniaturization, leading to smaller, more complex designs as compared to stationary oxygen concentrators. Therefore it is important that portable concentrator performance is monitored closely and that problems can be fixed quickly to avoid leaving patients stranded without oxygen supply. Conventional concentrator diagnostic testing devices are external units which have to be connected to the concentrator each time when used. The need to connect an external, stand-alone device to the concentrator is time consuming and adds to the complexity and inefficiency of the testing process. Accordingly, one of the objects of the present invention is to provide a built-in administrative and diagnostic testing functions for portable oxygen concentrators, which results in more informed decision making in device repair and increased up-time for portable oxygen concentrators.

SUMMARY OF THE INVENTION

One embodiment of the present invention relates to a portable oxygen concentrator. The concentrator generally includes a compressor which compresses a gas, such as air, to provide an output gas, a PSA unit which receives and processes the output gas from the compressor to produce a product gas, a product gas storage device for storing the product gas, and sensors for sensing one or more process parameters of the system. The concentrator further includes a multi-level user interface, wherein the user interface comprises user command functions and a display screen that is integrally formed with the concentrator. Preferably, the display screen has a first level which displays system setting information and a second level which displays system diagnostic information. The concentrator further includes a multiple mode programmable controller. Preferably, the controller has an operations mode in which the controller controls operation of the concentrator to produce the product gas in accordance with one or more system settings. Preferably, the controller has a diagnostic mode in which the controller performs one or more concentrator diagnostic functions and communicates diagnostic results to the user interface in a manner such that the results are displayed on the second level of the display screen as system diagnostic information.

In one embodiment, the diagnostic mode of the controller is activated in response to a triggering event, such as a user input command. In one implementation, the user input command comprises a combination of user inputs configured to inhibit accidental activation of the diagnostic mode. In another implementation, the diagnostic mode of the controller is activated when one or more of the process parameters deviate from a target or nominal range. In yet another implementation, the system diagnostic information on the second level of the display screen is displayed in an abbreviated code form.

In a preferred embodiment, the concentrator diagnostic functions performed by the controller in the diagnostic mode are selected from the group consisting of testing the PSA unit for leaks, testing the compressor performance at a given speed, testing operation of the valves in the concentrator, and testing the oxygen concentration level in the product gas produced. In one implementation, the controller performs the concentrator diagnostic functions by acquiring process parameter data from the sensors and calculating the data in accordance with selected operating parameters to determine if system repair is needed.

In another embodiment, the sensors are selected from the group consisting of product gas pressure sensor, compressor temperature sensor, product gas oxygen concentrator sensor, ambient pressure sensor, current sensor, battery temperature sensor, adsorbent bed temperature sensor, and power charge sensor. In another embodiment, the multi-level user interface comprises concealed command functions which can be activated by certain user input commands. In a preferred implementation, the concealed command functions comprise concentrator calibration functions and other functions which are preferably only accessible by technicians or other trained personnel.

Preferably, the administrative and diagnostic functions are integrated with the portable oxygen concentrator such that no external unit or device is required. Advantageously, a variety of complex diagnostic and testing functions are integrally incorporated into the concentrator design without substantially increasing the weight or size of the concentrator. In one implementation, the concentrator, including the administrative and diagnostic systems, weighs less than 10 pounds.

Another embodiment of the present invention relates a method of providing self-diagnostic capability for a portable oxygen concentrator using a programmable controller. The method comprises triggering the programmable controller to switch from an operations mode to a diagnostic mode and causing the controller to adjust a process variable of the concentrator to a predetermined level, measuring a parameter associated with the process variable, comparing measured value of the parameter with a nominal value range, communicating information to a user interface when the measured value deviates from the nominal value range and displaying the information on a display screen. In one implementation, communicating information to the user interface when the measured value deviates from the nominal value range comprises translating the information into a code, wherein the code is configured to indicate to users the nature of the malfunction associated with the deviation of the measured value. In one embodiment, adjusting the process variable of the concentrator to a predetermined level comprises increasing the pressure of a product gas storage device to a predetermined pressure level. In another embodiment, measuring a parameter associated with the process variable comprises utilizing one or more sensors to measure the internal pressure drop in the product gas storage device over a period of time. In yet another implementation, adjusting a process variable of the concentrator to a predetermined level comprises causes the compressor to operate at a predetermined speed. In yet another implementation, causing the controller to measure a parameter associated with the process variable comprises causing the controller to work with one or more sensors to measure the time interval for a predetermined pressure change to occur in the product storage device. In yet another implementation, adjusting a process variable of the concentrator to a predetermined level comprises causing the controller to trigger an auto bolus delivery at a predetermined rate. In yet another implementation, causing the controller to measure a parameter associated with the process variable comprises causing the controller to work with one or more sensors to measure the oxygen concentration of the oxygen delivered.

Another embodiment of the present invention relates to a gas fractionalization apparatus. The apparatus comprises a compressor, a PSA unit wherein the PSA unit comprises adsorbent beds, gas flow control, and exhaust, and a product gas storage device. The apparatus further comprises a plurality of sensors and a user interface comprising a display screen that is integrally formed with the apparatus and a programmable controller wherein the controller is responsive to at least one diagnostic mode command, wherein the controller obtains data from the sensors, wherein the controller displays system health information on the display screen upon initiation of the diagnostic mode command. In one implementation, the system health information displayed is selected from the group consisting of individual adsorbent bed pressure, ambient pressure, battery charge state, external power level, system current, actual product gas pressure, target product gas pressure, average product gas pressure, maximum product gas pressure, compressor temperature, battery temperature, PWM motor speed variation, and pressure signal generated by breathing pressure. In one implementation, one or more of the system health information displayed is in an encrypted form.

DETAILED DESCRIPTION OF THE PREFERRED EMBODIMENT

Figure 1:
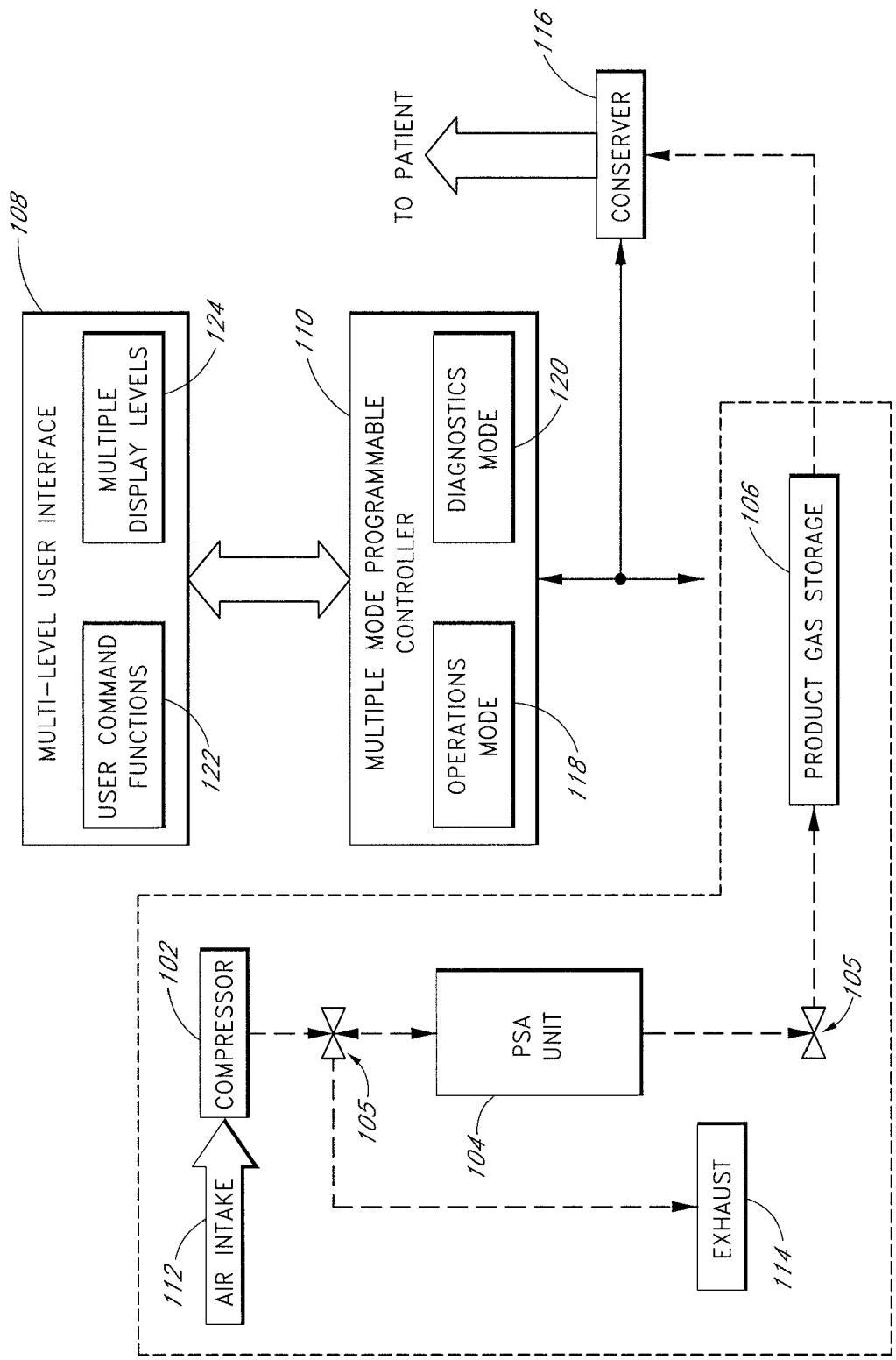
FIG. 1 is a block diagram of a gas fractionalization system of one embodiment of the present invention.

FIG. 1 schematically illustrates a gas fractionalization system 100 of one preferred embodiment of the present invention. The system 100 is applicable to a variety of gas concentrator implementations, such as portable oxygen concentrators. As shown in FIG. 1, the system 100 generally comprises a compressor 102 through which ambient air is drawn into the system 100 and pressurized, a PSA unit 104 which receives and processes the pressurized gas to produce a product gas having a higher oxygen content than the ambient air, valves 105 configured to regulate gas flow within the system in a known manner, a storage device 106 for storing the product gas, a multi-level user interface 108, and a multiple mode programmable controller 110. As to be described in greater detail below, the multiple mode programmable controller 110 controls and operation of various components of the system and is also capable of performing self-diagnostic functions to identify and communicate system performance and malfunctions. As also to be described in greater detail below, the multi-level user interface 108 includes user command functions and a multi-level display screen. The user command functions may comprise hidden user commands and the display screen has multiple levels, with certain levels only accessible by pre-approved users.

As illustrated in FIG. 1, the compressor 102 draws ambient air into the system 100 through an air intake 112 and compresses the air for use by the PSA unit 104. In one embodiment, the compressor 102 is a variable output compressor, capable of varying its speed and/or displacement, so as to be capable of operating with a fixed displacement and variable speed, a variable displacement and fixed speed, or a variable displacement and variable speed. In another embodiment, the compressor 102 is a non-reciprocating compressor such as that described in U.S. Pat. No. 5,759,020, which is hereby incorporated by reference in its entirety. In yet another embodiment, the compressor 102 is a linear compressor such as that described in U.S. Pat. No. 5,525,845, which is hereby incorporated by reference in its entirety. In a preferred implementation, the compressor 102 operates in a fixed displacement and variable speed mode. In further preferred implementations, the compressor may utilize brushed or brushless D.C. motors.

The PSA unit 104 accepts the pressurized gas from the compressor 102 to produce oxygen enriched product gas in accordance with one or more PSA cycles. The general operating principles of PSA cycles are known and commonly used to selectively remove one or more components in various gas fractionalization devices such as oxygen concentrators. A typical PSA cycle entails cycling a valve system connected to at least two adsorbent beds such that a pressurized feed gas is sequentially directed to each adsorbent bed for selective adsorption of a component of the gas, while waste gas from previous cycles is simultaneously purged from the adsorbent bed(s) that are not performing the adsorption through an exhaust 114. Product gas with a higher concentration of the un-adsorbed components(s) is collected for use. Additional background information on PSA technology is described in U.S. Pat. No. 5,226,933, which is hereby incorporated by reference in its entirety. Additional details on gas fractionalization systems are also described in a U.S. Patent Application Publication No. 2005/0072426, which is hereby incorporated by reference in its entirety.

The product gas produced by the PSA unit 104 is directed to the storage device 106. The storage device 106 may comprise a storage vessel, a tank, an accumulator, a tube filled with a powder with a high area to volume ratio, or other enclosures effective for holding a volume of pressurized gas. Many concentrators used for therapeutic applications also include a conserver device 116, which controls and meters the delivery of oxygen gas to the patient in response to sensed breath.

As FIG. 1 further shows, the multiple mode programmable controller 110 has an operations mode 118 and a diagnostics mode 120. In the operations mode, the controller 110 controls operation of the apparatus to produce a product gas in accordance with the system settings. In the diagnostic mode 120, the controller 110 performs one or more system diagnostic functions and communicates diagnostic results to the multi-level user interface 108. The diagnostic functions can include but are not limited to testing the PSA unit for leaks, testing the compressor performance at a given speed, testing operation of valves in the concentrator, and testing the oxygen concentration level in the product gas produced. As described in greater detail below, in certain preferred embodiments, the controller 110 performs the diagnostic functions by acquiring process parameter data from a plurality of sensors disposed throughout the system and calculating data in accordance with selected operating parameters to determine if system maintenance or repair is needed.

In one embodiment, the diagnostic mode 120 of the controller 110 can be activated in response to a triggering event such as when a user input a command, or when one or more process parameters deviate from a target range, or when the system is scheduled to perform periodic self-diagnostic tests. In some implementations, the user input command can be in the form of a combination of user inputs so as to inhibit accidental activation of the diagnostic mode. As also shown in FIG. 1, the user interface 108 preferably comprises user command functions 122 and multiple display levels 124. In one implementation, the multiple display levels are embodied in a display screen that is integrally formed with the apparatus. In one embodiment, a first display level is adapted to display system setting information and a second display level is adapted to display system diagnostic information provided by the controller. In certain preferred embodiments, the system diagnostic information is displayed in an abbreviated code form so that only technicians and other trained personnel are able to interpret the meaning of the codes displayed. In other embodiments, the user command functions 122 include concealed command functions which only technicians and other trained personnel are able to access these command functions. In one version, the conceal command functions can include functions that would trigger calibration of the system or that would activate the diagnostic mode of the controller.

Figure 2:
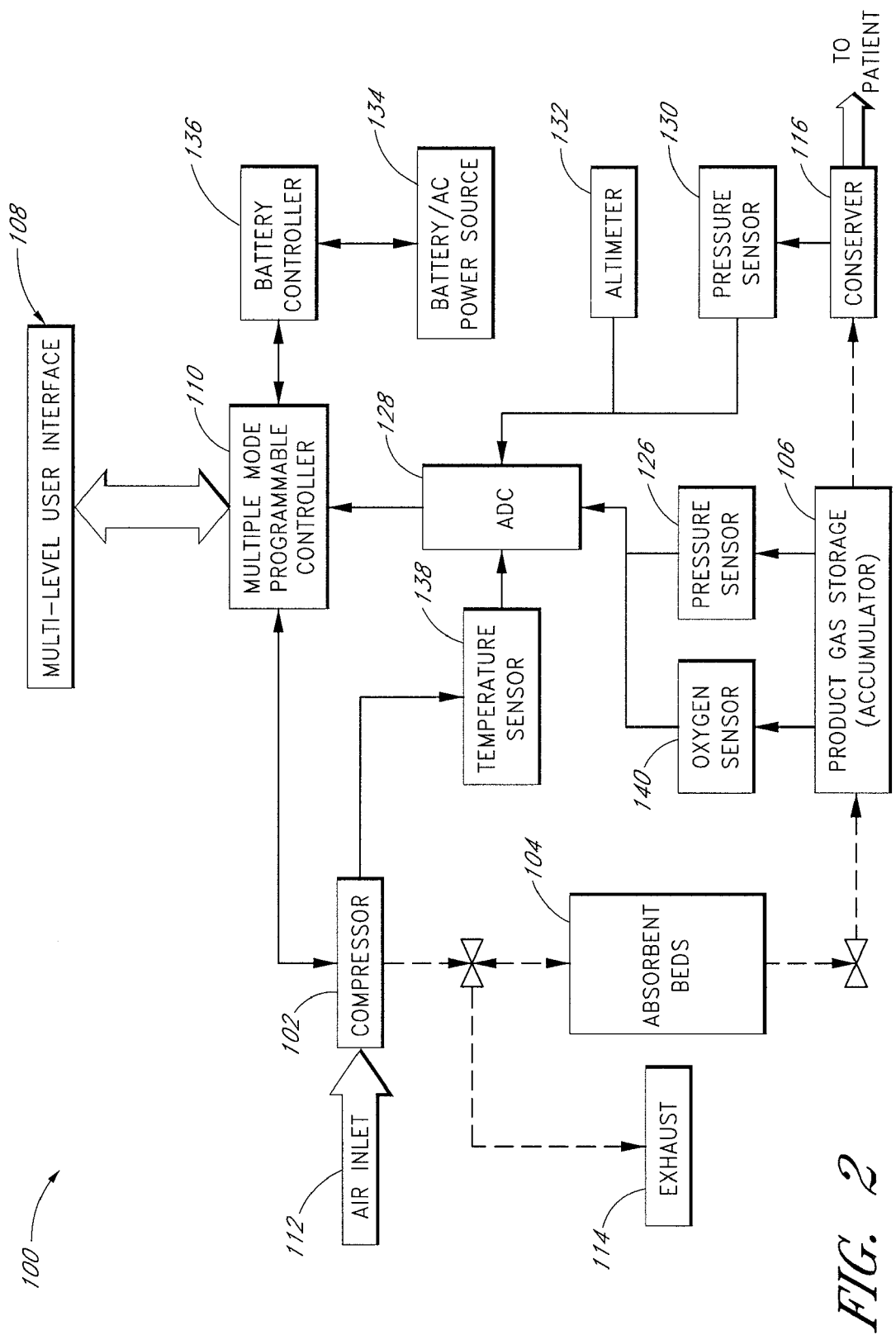
FIG. 2 is a block diagram of a gas fractionalization system of another embodiment of the present invention.

In some embodiments, the system 100 includes a plurality of sensors which operate in conjunction with the multiple mode programmable controller 110 to perform monitoring and diagnostic functions on the system. As shown in FIG. 2, a pressure sensor 126 is preferably installed to measure pressure in the product gas storage vessel 106, which in one embodiment is an accumulator. In other embodiments, the pressure sensor 126 can be installed at some other point in the system such as the compressor outlet. However the pressure sensor at the product storage vessel locates the pressure sensor within the network of valves in the system, and therefore provides a monitor of the many aspects of concentrator performance, such as seals, valves, filters etc. Thus the location in the product storage vessel is particularly suitable for diagnostic purposes.

Also shown in FIG. 2 are a variety of other sensing and monitoring devices. These devices may be sensors with analog output, which requires the controller 110 to acquire the data through Analog-to-Digital Converters 128, ADC, which may be a multiple channel device accepting many inputs. The ADC 128 may be a device that interfaces to the controller 110, or a built-in part of the controller itself, which many have many channels of analog input. Examples of sensors which will route to an ADC include thermistors for measuring temperature and pressure sensors. Other sensor data may be received from integrated sensor/digital devices which provide the data to the controller in digital form. Examples of the second type of sensors are temperature, charge and voltage sensors in a battery controller module. A wide variety of types of sensors, and input methods are contemplated by the invention, and the arrangement shown in FIG. 2 is exemplary rather than limiting.

Examples of sensors as shown in FIG. 2 are: conserver pressure sensor 130, altimeter or ambient pressure sensor 132, battery/power source sensing 134 and 136, compressor temperature 138, and oxygen concentration sensor 140. In a preferred embodiment, the sensors are read by the controller 110 either by ADC or other communication means, such as $I^2C$. Other inputs may include relative humidity sensors, user selectable setting values, external and internal communications status detectors, motion or acceleration sensors, sensors to measure patient physiological parameters (such as blood oxygen saturation levels), adsorbent temperature sensors, and global positioning devices. With the sensors shown by way of example, along with other operating parameters of the concentrator, the controller is capable of deriving many indices that indicate the concentrator system health. With the sensors shown, along with the compressor control data, such as PWM rate for example, the controller can derive at least the following:

individual adsorbent bed pressure;
ambient pressure;
battery charge state;
external power status (DC input voltage);
system electrical current;
actual product gas pressure;
target product gas pressure;
average product gas pressure;
maximum product gas pressure (at various points in the PSA cycle);
compressor temperature;
battery temperature;
compressor speed.

Such information can assist a technician in very quickly determining the type and cause of most concentrator problems. Thus a preferred embodiment of the invention is to include the sensing, processor power, software and control features with an appropriate user interface to create a powerful diagnostic capability particularly suitable for portable concentrators.

Figure 3:
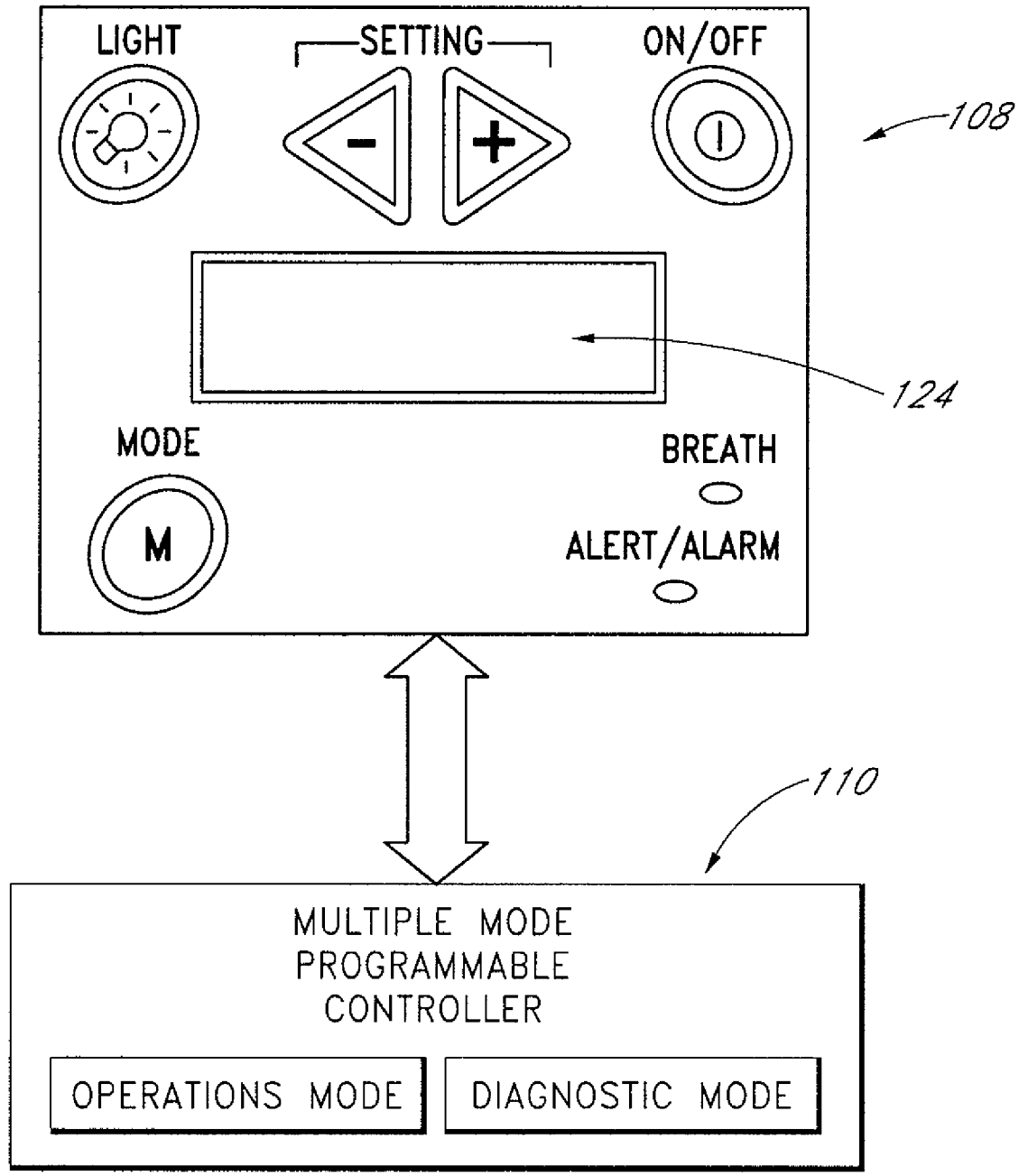
FIG. 3 illustrates a multi-level user interface of one implementation of the present invention.

FIG. 3 illustrates an implementation of the multi-level interface 108 of one preferred embodiment of the present invention. As shown in FIG. 3, the user interface 108 comprises a display screen 124, preferably an LCD display. The display screen 124 preferably has more than one level such that a first level shows information for the user such as mode flow setting. However, if a control panel sequence, such as a particular combination of input command not typical for normal operation, is initiated, the diagnostic or administrative mode of the system may be accessed. In the diagnostic mode, the display screen 124 displays a second level, which communicates various system diagnostic data as shown in FIG. 3. As shown, the numbers on the screen 124 represent values for one or more parameters related to system performance. In some embodiments, at least some of the displayed diagnostic data are unlabeled and partially reduced. In one implementation, the data on the screen 124 represents a combination of analog to digital conversion values, converted unit values, and hexadecimal register values representative of the various parameters. Patients may be asked to enter the diagnostic mode and read back portions of the data should a problem arise; this presentation of data provides useful information to the service personnel while limiting untrained persons from attempting diagnosis for which they are not trained. It may also alleviate stress in patients which may occur should they see and be able to interpret values which may vary somewhat during a system transient.

The preferred embodiments of the present invention have utility in at least two situations. During assembly and testing at the factory, many performance features can be determined readily by entering the diagnostic mode, rather than running specific tests with external equipment. Significant value also exists for use of the invention in the field. A patient with a portable concentrator may not have another source of oxygen either at home or when moving about. Thus the concentrator may be used 24 hours a day. If the patient, or caregiver, suspects a problem with the concentrator, the diagnostic screen will often immediately tell a technician if there is a problem. Since many problems have to do with external or operational issues such as hose connections, settings or the like, often the screen will allow the technician to solve the problem immediately, thereby eliminating a significant amount of concentrator downtime and cost to the caregiver of servicing the unit in the field that would occur without the availability of the information provided in the diagnostic mode.

In the system shown and described, one display screen with all of the data is shown. In some preferred embodiments, multiple levels of commands with associated higher detailed screens are contemplated as well. In one embodiment, a set of user interface inputs, such as a coordinated set of button pushes, may access a selectable menu of available diagnostic screens and/or functions. The diagnostic capability is also useful for monitoring aging and calibration of the concentrator, even if no problem is reported. The screen also provides a quick way to determine if a concentrator returned to the provider by one patient, when no longer needed, can be provided to another without the need for return to the factory. As an extension of this system, it may be possible to display the real time (or time averaged) data on an auxiliary display, including a palm pilot or a laptop computer, via wireless communications methods such as IrDA or RF transmission.

A further diagnostic capability, useful for factory check, field returns and periodic system health checks is enabled by the elements of the invention. In addition to reporting parameters during normal operation as described above, in another embodiment, actual specific test sequences are run by the controller, typically during a time when the concentrator is not in use, and the sensor and associated derived data are used to make a detailed check on an aspect of system health. Listed below are examples of diagnostic tests performed by the controller.

In one embodiment, a diagnostic test performed by the controller relates to testing the manifold, adsorbent beds, gaskets, and valve interfaces for leaks. This leak diagnostic test comprises a first step in which the controller causes the compressor to pressurize the product gas storage device to a predetermined set pressure level, as sensed by a product gas pressure sensor, and cause appropriate valve(s) to be closed. The test proceeds with a second step in which the controller monitors the internal pressure drop over a set time period, such that pressure drops below a defined level would fail the test. The first and second steps may be repeated, isolating specific pneumatic areas of the device for pressure drop measurement. If the controller determines that the pressure drops are outside a nominal range, the controller will communicate such information to the user interface.

In another embodiment, a diagnostic test performed by the controller relates to testing the motor/compressor performance at a given speed and pressure. The motor/compressor performance test comprises a first step in which the controller causes the compressor to run at a predetermined speed (RPM), a second step in which the controller measures the time it takes for a predefined pressure change in the product gas pressure as sensed by an product gas pressure sensor. The test further includes a third step in which the controller compares the time it takes for such pressure change in a known good compressor as a way of rating the installed compressor performance. The test can also include a fourth step in which the controller measures system power to determine if the compressor is operating properly when running at a known nominal speed and pressure. In one implementation, if the controller determines that the compressor performance deviates from the nominal range at a given speed and pressure, the controller will communicate such information to the user interface so that the information can be displayed on the display screen.

In yet another embodiment, a diagnostic test performed by the controller relates to testing the ability of valves to open/close and valve drive capability. The valve capability test comprises a first step in which the controller causes the compressor to pressurize adsorbent beds in the PSA unit, a second step in which the controller causes a selected set of valves to open and close, a third step in which the controller monitors a product gas pressure sensor for a corresponding expected pressure change. In one implementation, if the controller determines that the pressure detected deviates from the nominal range of expected pressure change, the controller will communicate such information to the user interface. The information can indicate that there might be malfunctions of one or more valves. In another implementation, the information can also pinpoint the malfunction valves to a particular component of the system.

In yet another embodiment, a diagnostic test performed by the controller relates to testing the ability of the concentrator to produce reasonable oxygen concentration levels within a certain period of time. The test comprises a first step in which the controller initiates a PSA cycle at a given flow setting and wait for a set time period. The test continues with a second step in which the controller reading a product gas oxygen sensor to determine whether oxygen concentration is within a predefined known nominal range after this time period, as compared to known good concentrators. In one implementation, if the controller determines that the oxygen concentration is outside the predetermined known nominal range, the controller will communicate the information to the multi-level user interface, which will in turn display the information on the display screen.

Additional diagnostic tests are contemplated, which can also be run, by access to hidden commands, either in the field or at the factory. In one embodiment, autofiring boluses while monitoring oxygen concentration is a method for running the concentrator in manufacturing and other isolated cases such as when a provider receives a unit and wants to check to determine that oxygen concentration is maintained while delivering the prescribed flow of gas. In a preferred implementation of this test, at least three different bolus delivery rates are selectable in order to test the device under different rates of delivery. Additionally, a test may be included allowing a bolus to be manually triggered. In one embodiment, an option may be accessible from an administrative modes menu, some other button press, or combination of user inputs allowing a technician to select manual bolus triggering. The interface may then allow the user to select a bolus volume to deliver. For example, the user may be able to increment or decrement the target bolus volume. An additional button press may trigger the bolus delivery.

Alternatively, the user may be able to select a bolus delivery rate, and a subsequent button press may trigger either a single bolus delivery of the appropriate corresponding volume, or a sequence of bolus deliveries. As a further tool, the device may be configured to have a manual bolus delivery trigger in normal operation. For example, in normal operation a bolus would be fired when a specific combination of button presses or user inputs is made. Another useful hidden command function contemplated is calibration of pressure and/or oxygen concentration sensors. In certain embodiments, some sensors may have an offset built in, and that by calibrating the system, a more accurate measurement can be made. Calibration of the pressure sensor is performed at atmospheric pressure with the concentrator unpressurized which involves comparing the product gas pressure sensor to an ambient pressure sensor. The internal pressure sensor can also be correlated to the output value seen on the ambient pressure transducer. Calibration of the oxygen sensor may be performed by first flushing the system with room air (in such a way as to provide no gas separation), measuring the oxygen sensor output (and potentially the ambient pressure sensor output if necessary), and adjusting the calibration such that the processor interprets the signal value as approximately a percentage such as 21%. Because some sensors may have characteristic drift over time, this feature is useful in testing for this drift and resetting the sensor offset.

Both the diagnostic display on the user interface and diagnostic mode of the controller offer reliability, operability, and cost advantages to portable concentrators. Increased uptime is achieved due to faster problem resolution and the capture of aging problems before failure. Decreased costs are achieved by more efficient initial test and assembly, and less need to return units to the factory. Overall the invention is a significant contributor to practical and economic utility for portable concentrators.

Although the above-disclosed embodiments have shown, described, and pointed out the fundamental novel features of the invention as applied to the above-disclosed embodiments, it should be understood that various omissions, substitutions, and changes in the form of the detail of the devices, systems, and/or methods shown may be made by those skilled in the art without departing from the scope of the invention. Consequently, the scope of the invention should not be limited to the foregoing description, but should be defined by the appended claims.

What is claimed is:

1. A method of providing self-diagnostic capability for a portable oxygen concentrator using a programmable controller, comprising:

triggering the programmable controller to switch from an operational mode to a diagnostic mode; and causing the controller to adjust a process variable of the concentrator to a predetermined level, measure a parameter associated with said process variable, compare measured value of the parameter with a nominal value range, communicate information to a user interface when said measured value deviates from said nominal value range; and display the information on a display screen, wherein communicating information to the user interface when said measured value deviates from said nominal value range comprises translating said information into an abbreviated code, said abbreviated code is configured to indicate to users the nature of the malfunction associated with the deviation of the measured value, wherein causing the controller to measure a parameter associated with said process variable comprises causing the controller to work with one or more sensors to measure the internal pressure drop in the product gas storage device over a period of time, wherein causing the controller to measure a parameter associated with said process variable further comprises causing the controller to work with one or more sensors to measure the time interval for a predetermined pressure change to occur in the product storage device.

2. The method of claim 1, wherein causing the controller to adjust said process variable of the concentrator to a predetermined level comprises causing the controller to increase the pressure of a product gas storage device to a predetermined pressure level.

3. The method of claim 1, wherein causing the controller to adjust a process variable of the concentrator to a predetermined level comprises causing the controller to operate the compressor at a predetermined speed.

4. The method of claim 1, wherein causing the controller to adjust a process variable of the concentrator to a predetermined level comprises causing the controller to trigger an auto bolus delivery at a predetermined rate.

5. The method of claim 1, wherein causing the controller to measure a parameter associated with said process variable further comprises causing the controller to work with one or more sensors to measure the oxygen concentration of the oxygen delivered.

* * * * *